United States Patent
Ishizaki et al.

(10) Patent No.: US 7,740,013 B2
(45) Date of Patent: Jun. 22, 2010

(54) OXYGEN CONCENTRATING APPARATUS AND EXECUTION SUPPORT METHOD OF HOME OXYGEN THERAPY USING THE SAME

(75) Inventors: Takayuki Ishizaki, Yamaguchi (JP); Tadashi Miyazaki, Tokyo (JP); Yoichi Okabe, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1141 days.

(21) Appl. No.: 10/567,924

(22) PCT Filed: Aug. 12, 2004

(86) PCT No.: PCT/JP2004/011865

§ 371 (c)(1),
(2), (4) Date: Feb. 10, 2006

(87) PCT Pub. No.: WO2005/016426

PCT Pub. Date: Feb. 24, 2005

(65) Prior Publication Data

US 2007/0023039 A1      Feb. 1, 2007

(30) Foreign Application Priority Data

Aug. 14, 2003   (JP) ............................. 2003-293353

(51) Int. Cl.
A61M 11/00   (2006.01)

(52) U.S. Cl. .............................. 128/204.21; 128/204.18

(58) Field of Classification Search ............ 128/204.23, 128/204.21, 204.18, 202.22, 205.23; 600/529–543
See application file for complete search history.

(56) References Cited

U.S. PATENT DOCUMENTS

| 5,233,987 | A | * | 8/1993 | Fabian et al. .................. 607/41 |
| 5,517,983 | A |   | 5/1996 | Deighan et al. |
| 5,706,801 | A | * | 1/1998 | Remes et al. .......... 128/202.26 |

(Continued)

FOREIGN PATENT DOCUMENTS

JP       62-270170 A       11/1987

(Continued)

OTHER PUBLICATIONS

International Search Report, Nov. 16, 2004.

(Continued)

*Primary Examiner*—Steven O Douglas
(74) *Attorney, Agent, or Firm*—Rader, Fishman & Grauer PLLC

(57) ABSTRACT

In order to enable a medical worker to certainly and easily know whether a patient on a home oxygen therapy, who continues to inhale an oxygen-enriched gas at home, performs the inhalation as prescribed, a history of a supply condition of the oxygen-enriched gas supplied to the patient is recorded and held as supply history information, this supply history information is compared with a prescription of the oxygen therapy of the patient to generate patient's compliance information to indicate the degree to which the oxygen therapy is performed in accordance with the prescription, the oxygen concentrating apparatus is constructed to be portable, and a doctor can confirm the patient's compliance information at the time of going to a medical institution regularly.

9 Claims, 2 Drawing Sheets

U.S. PATENT DOCUMENTS

| | | | |
|---|---|---|---|
| 6,332,463 B1 * | 12/2001 | Farrugia et al. | 128/204.18 |
| 6,910,481 B2 * | 6/2005 | Kimmel et al. | 128/204.23 |
| 7,469,697 B2 * | 12/2008 | Lee et al. | 128/200.24 |

FOREIGN PATENT DOCUMENTS

| | | | |
|---|---|---|---|
| JP | 02-088078 A | 3/1990 |
| JP | 03-143451 A | 6/1991 |
| JP | 05-071894 B2 | 10/1993 |
| JP | 10-052407 A | 2/1998 |
| JP | 08-504624 A | 5/1998 |
| JP | 11-314903 A | 11/1999 |
| JP | 2002-214012 A | 7/2002 |
| JP | 2002-272845 A | 9/2002 |
| JP | 2003-062076 A | 3/2003 |
| JP | 2003-175107 A | 6/2003 |
| WO | WO-94/13349 | 6/1994 |

OTHER PUBLICATIONS

International Search Report dated Nov. 16, 2004.
JPO Office Action, App. No. 2005-513208, Dec. 1, 2009 (3 pages).
Office Action of Japanese Patent Application No.: 2005-513208 mailed on Feb. 24, 2009 (Japan).

* cited by examiner

OXYGEN CONCENTRATING APPARATUS AND EXECUTION SUPPORT METHOD OF HOME OXYGEN THERAPY USING THE SAME

TECHNICAL FIELD

The present invention relates to an oxygen concentrating apparatus and an execution support method of a home oxygen therapy, and particularly to a structure in which it is possible to certainly and easily know whether a patient on home oxygen therapy, who continues to inhale an oxygen-enriched gas at home, performs the inhalation as prescribed.

BACKGROUND ART

Hitherto, for a patient with a respiratory disease, a breathing gas supplying apparatus (hereinafter also referred to as an oxygen concentrating apparatus) for obtaining an oxygen-enriched gas by separating and concentrating atmospheric oxygen has been developed, and an oxygen therapy using the same has gradually become popular.

Although there is a case where the oxygen therapy is performed while the patient enters a medical institution, in the case where the respiratory disease of the patient becomes chronic, and it is necessary that the oxygen therapy is performed over a long period of time to calm and stabilize the symptom, a medical treatment is also performed in which the oxygen concentrating apparatus is installed in the patient's home, the oxygen-enriched gas supplied by this oxygen concentrating apparatus is guided to the vicinity of the nasal cavity of the patient by using a tube member called a cannula, and the patient inhales it. This kind of medical treatment is especially called a domiciliary oxygen therapy or HOT (Home Oxygen Therapy).

Since the home oxygen therapy was covered by insurance in 1985 in Japan, this has been prescribed mainly for the chronic obstructive pulmonary disease (COPD) and tuberculosis sequela, and the rough number of patients is 60 to 65 per hundred thousand persons in Japan and there are about eighty thousand persons (as of 2000). The old Welfare Ministry respiratory failure section and the like report that this home oxygen therapy improves the vital prognosis of the patient. It is inferred that the reason why the home oxygen therapy is effective is that the pulmonary circulation dynamics is improved with the improvement of anoxemia.

The home oxygen therapy is performed in steps of (1) doctor's medical examination of a patient, (2) doctor's issuance of a home oxygen therapy execution written directive describing a prescription to the patient based on the medical examination, (3) installation of an oxygen concentrating apparatus in a patient's home based on the written directive, (4) continuous execution of inhalation of an oxygen-enriched gas using the oxygen concentrating apparatus, and (5) medical examination at the time of a hospital visit which is made regularly, for example, once a month.

DISCLOSURE OF THE INVENTION

When the home oxygen therapy is started, the doctor issues the written directive as described above, and the prescription of the home oxygen therapy to be received by the patient is written on this written directive. The prescription contains (1) the oxygen concentration of the oxygen-enriched gas to be supplied to the patient, (2) the use flow rate and use time of the oxygen-enriched gas to be supplied to the patient, and the like. On the other hand, since the inhalation of the oxygen-enriched gas is performed in the patient's home or at the place where the patient has gone, the doctor can not directly confirm whether the inhalation is performed and the conditions of gas supply at the site where the inhalation is performed.

Then, it is necessary that the doctor asks the patient about his/her condition at the time of treatment as an outpatient, which is performed regularly, for example, once a month, and confirms whether the inhalation is performed as prescribed. However, the patient can give an answer different from the actual situation to the doctor's inquiry.

Based on the result of the medical examination of the patient at the time of the hospital visit, the result of the check, the result of the inquiry and the like, the doctor confirms the therapy effect of the home oxygen therapy and makes a future therapy plan, and therefore, it becomes a significant obstacle in continuing the home oxygen therapy that the answer of the patient to the inquiry can be different from the fact.

Then, in addition to the inquiry to the patient, some methods have been conventionally proposed which enable objective confirmation of a situation in which the patient actually inhales the oxygen-enriched gas. For example, a breathing gas supplying system and apparatus proposed by the present applicant and disclosed in JP-A-3-143451 is constructed such that the breathing gas supplying apparatus (corresponding to the oxygen concentrating apparatus) is provided with information collecting means, the information collecting means collects and stores information including the oxygen concentration of gas to be supplied and the flow rate, and transmission means provided in the breathing gas supplying apparatus transmits it to external specified receiving means through a telephone line or the line.

However, according to the conventional structure, it is necessary to provide the transmission means of the information in the oxygen concentrating apparatus, and it is necessary to provide the telephone line, wireless transmission path or the like between the oxygen concentrating apparatus and a specified monitoring center or the like, and further, with respect to the information received by the monitoring center, transfer through transmission, mailing, manual delivery or the like must be performed so that it can be used by the doctor and the like when the patient goes to the hospital, and therefore, the management steps are needed, and the communication cost for transmission/reception is produced.

Besides, as a structure which can be easily achieved from the above-mentioned related art structure, when a structure is adopted in which the information stored by the information collecting means is not transmitted through the transmission path, but is collected from each oxygen concentrating apparatus in such a manner that the person in charge, who visits the patient's home regularly, reads the display screen or transfers the information to a carried portable information terminal, the burden of providing and managing the transmission path (communication path) of the information is eliminated, however, the labor cost of the person in charge of information collection, the management cost and the like remain.

The invention has been made in view of the above circumstances, and has an object to provide an oxygen concentrating apparatus which enables a medical worker to certainly and easily know whether a patient on a home oxygen therapy, who continues to inhale an oxygen-enriched gas at home, performs the inhalation as prescribed, and an execution support method of a home oxygen therapy.

In order to solve the problem, the invention provides an oxygen concentrating apparatus having respective structures recited in under-mentioned items 1) to 11) and an execution support method of a home oxygen therapy using the same.

1) In an oxygen concentrating apparatus which can be carried by a user, and separates atmospheric oxygen to supply it to the user at least during movement of the user, the oxygen concentrating, apparatus is characterized by comprising recording means for recording a supply condition of an oxygen-enriched gas supplied to the user, and output means or display means for enabling the recorded supply condition of the oxygen-enriched gas to be confirmed in a medical institution where regular outpatient treatment is received.

2) The oxygen concentrating apparatus as recited in item 1), characterized by comprising prescription supply condition input means for inputting a supply condition prescribed for the user, and arithmetic means for calculating a patient's compliance by comparing the recorded supply condition with the prescribed supply condition.

3) The oxygen concentrating apparatus as recited in item 1) or 2), characterized in that the recording means is means for recording a supply condition of at least one of a supply flow rate set value of the oxygen-enriched gas, an actually measured value of a supply flow rate, and a history record of supply time.

4) The oxygen concentrating apparatus as recited in any one of items 1) to 3), comprising means for detecting whether a patient breathes, wherein the recording means is means for recording a breath detection result.

5) The oxygen concentrating apparatus as recited in any one of items 2) to 4), wherein the arithmetic means is means for calculating the patient's compliance of at least one of an average use time, an average use flow rate, an average exercise ratio, an average synchronous flow rate, an average continuous flow rate, a breath sensing ratio, an exercise time breath sensing ratio, and an apparatus nonuse day count.

6) The oxygen concentrating apparatus as recited in any one of items 2) to 4), wherein the arithmetic means is means for calculating a change of the patient's compliance of at least one of a use time, a use flow rate, an exercise ratio, a synchronous flow rate, a continuous flow rate, a breath sensing ratio, and an exercise time breath sensing ratio in a specified period or a change thereof in a specified period unit.

7) An execution support method of a home oxygen therapy comprises recording a supply condition of an oxygen-enriched gas supplied to a home oxygen therapy patient by a carried oxygen concentrating apparatus, and outputting or displaying the recorded supply condition of the oxygen-enriched gas in a medical institution into which the oxygen concentrating apparatus is carried and in which regular outpatient treatment is received.

8) An execution support method of a home oxygen therapy comprises recording a supply condition of an oxygen-enriched gas supplied to a home oxygen therapy patient by a carried oxygen concentrating apparatus, comparing the recorded supply condition with a supply condition previously prescribed for the patient to calculate a patient's compliance, and outputting or displaying the calculated patient's compliance.

9) An execution support method of a home oxygen therapy comprises recording a supply condition of an oxygen-enriched gas supplied to a home oxygen therapy patient by an oxygen concentrating apparatus and a detection result as to whether the patient breathes at time of supply, comparing the recorded supply condition with a supply condition previously prescribed for the patient to detect a patient's observance state of a prescription condition and to detect whether the apparatus is used, and calculating a patient's compliance.

10) The execution support method of the home oxygen therapy as recited in item 9), wherein the patient's compliance is patient's compliance information of at least one of an average use time of the oxygen concentrating apparatus, an average use flow rate, an average exercise ratio, an average synchronous flow rate, an average continuous flow rate, a breath sensing ratio, an exercise time breath sensing ratio, and an apparatus nonuse day count.

11) The execution support method of the home oxygen therapy as recited in item 9), wherein the patient's compliance is a change of the patient's compliance of at least one of a use time of the oxygen concentrating apparatus, a use flow rate, an exercise ratio, a synchronous flow rate, a continuous flow rate, a breath sensing ratio, and an exercise time breath sensing ratio in a specified period or a change thereof in a specified period unit.

BEST MODE FOR CARRYING OUT THE INVENTION

Figure 1:
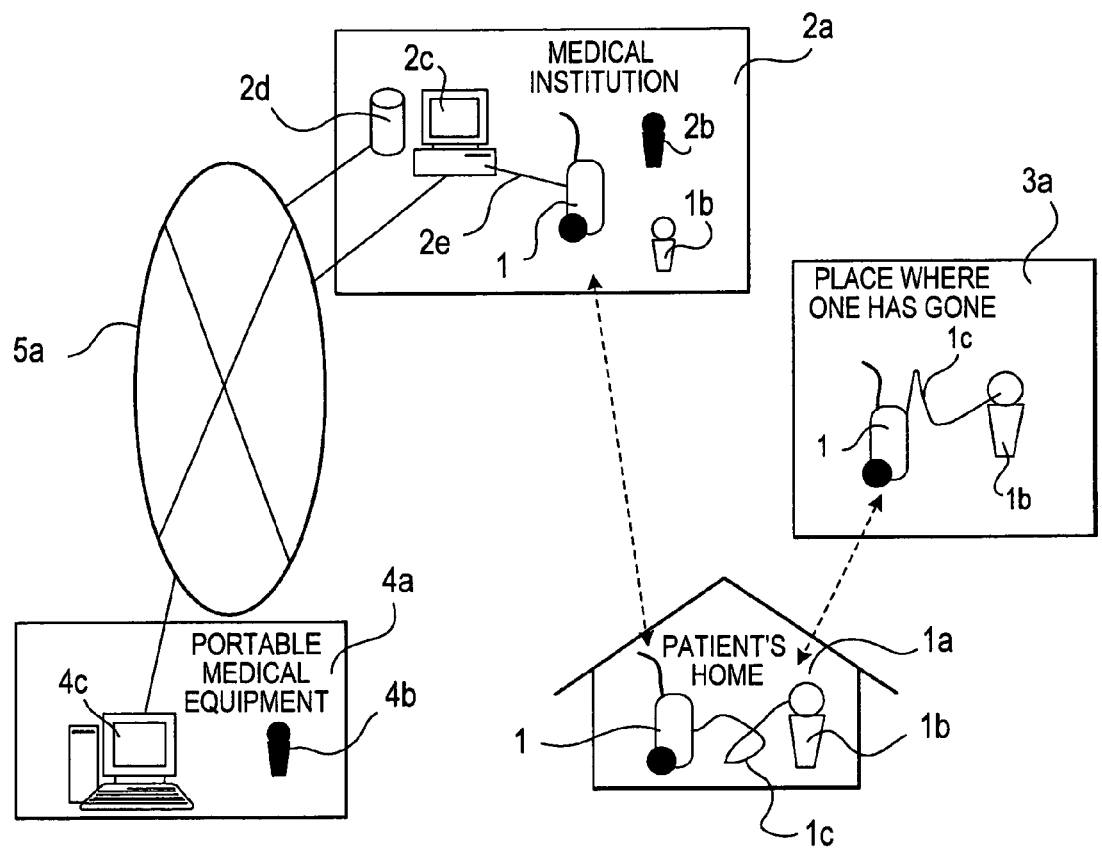
FIG. 1 is a connection view of an oxygen concentrating apparatus of an embodiment of the invention.
Figure 2:
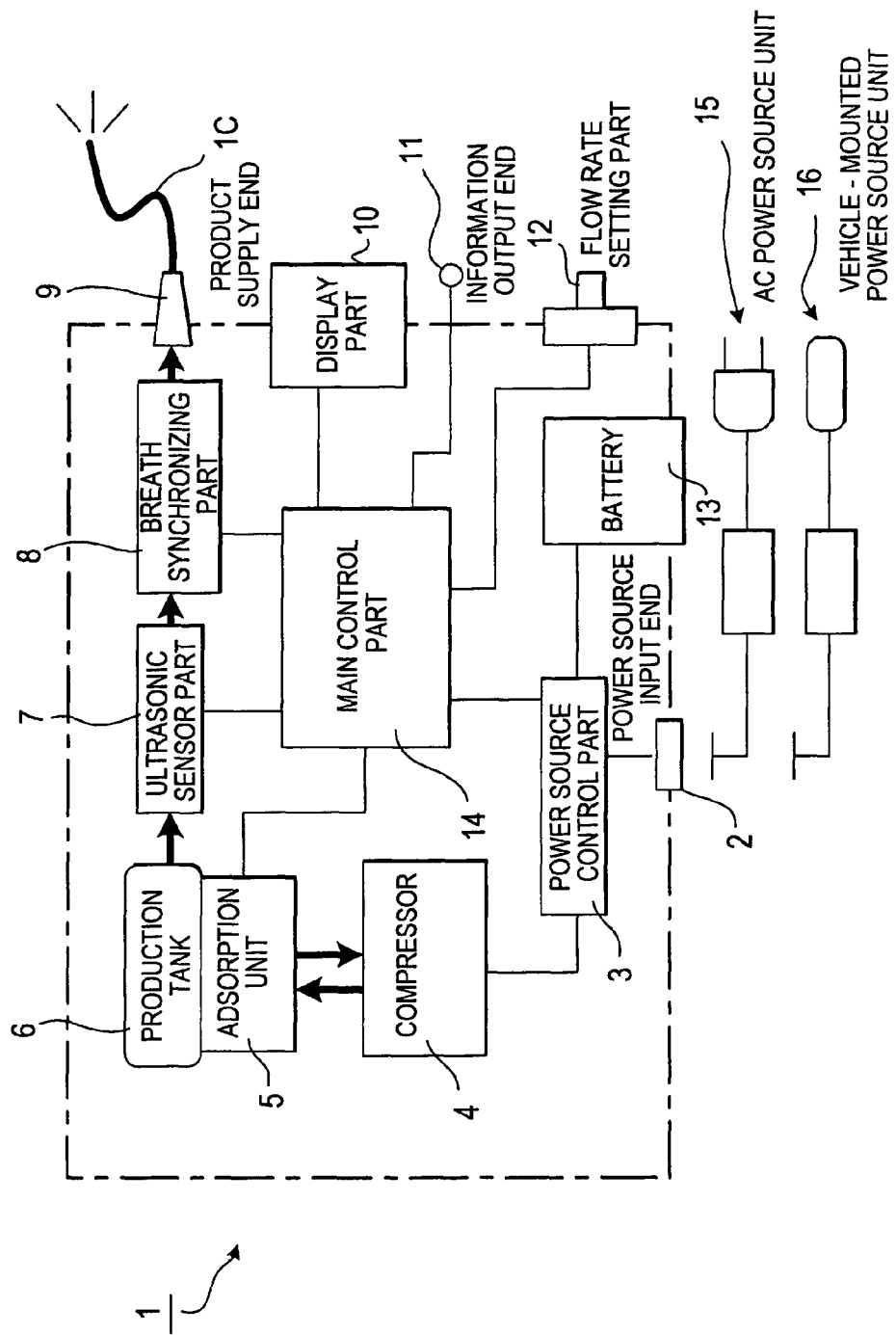
FIG. 2 is a structural view of the oxygen concentrating apparatus of FIG. 1.

Hereinafter, an oxygen concentrating apparatus of a preferred example of an embodiment of the invention will be described with reference to FIG. 1 and FIG. 2. FIG. 1 is a connection view of the oxygen concentrating apparatus of the preferred example of the embodiment of the invention, and FIG. 2 is a structural view of the oxygen concentrating apparatus of FIG. 1.

[Structure of Oxygen Concentrating Apparatus]

As described before, an oxygen concentrating apparatus 1 of this example is an apparatus which is used mainly for the home oxygen therapy, and separates atmospheric nitrogen and supplies high concentration oxygen (oxygen-enriched gas), and is a pressure fluctuation adsorption type oxygen concentrating apparatus in which as an adsorbent capable of adsorbing nitrogen preferentially- to oxygen, for example, molecular sieve zeolite 5A, 13X, lithium zeolite or the like is filled in an adsorption tube (adsorption unit 5), and pressurized air made by an air compressing apparatus (compressor 4) is supplied, so that oxygen is extracted.

Incidentally, when the invention is carried out, the structure of the oxygen concentrating apparatus relating to the basic oxygen concentrating function is not limited to the mode described here, and an already known structure or various structures proposed in future can be adopted.

As shown in the structural view of FIG. 2, the oxygen concentrating apparatus 1 of this embodiment as the pressure fluctuation adsorption type oxygen concentrating apparatus supplies the pressurized air compressed by the compressor 4 from the atmosphere to the adsorption tube (included in the adsorption unit 5) filled with the adsorbent to adsorb nitrogen preferentially to oxygen, brings the inside of the adsorption tube into a pressurized state to adsorb nitrogen, and extracts oxygen not adsorbed. The oxygen-enriched gas extracted from the adsorption tube and mainly including oxygen is stored in a production tank 6, and then is supplied from a product supply end 9 to the outside of the apparatus 1 through an ultrasonic sensor part 7 and a breath synchronizing part 8, and is supplied to a user (home oxygen therapy patient) through a nasal cannula 1c which is a tube member to transport the oxygen-enriched gas from the oxygen concentrating apparatus 1 to the vicinity of the nasal cavity of the patient.

Here, with respect to the adsorbent, since the amount of nitrogen which can be adsorbed in one process is determined by the amount of the adsorbent and the kind thereof, before the amount of nitrogen adsorbed by the adsorbent is saturated, a flow path switching valve is switched to expose the adsorbent tube to the atmosphere, the pressure of the inside of the adsorbent tube is reduced to desorb nitrogen, and the adsorbent is regenerated. Besides, the flow path switching valve is controlled by a main control part 14 so that it is switched according to a previously set time. Incidentally, in order to increase the amount of adsorption/desorption in one process, the inside of the adsorption tube in the desorption process may be made vacuous by using a vacuum pump.

Incidentally, in order to realize the oxygen concentrating apparatus 1 of this embodiment as a portable one, which is not fixedly installed in the patient's home, by reducing the size and weight, it is a desirable mode that for example, a structure disclosed in Japanese Patent No. 3269626 is used, and the adsorption unit 5 includes rotation valve means in which a gas flow path for pressurization and desorption to plural adsorption tubes is successively continuously formed.

As disclosed in JP-A-2002-214012 filed by the present applicant, the ultrasonic sensor part 7 measures propagation speeds of two sound waves, for example, ultrasonic waves in the same direction as and the reverse direction from a direction in which the oxygen-enriched gas flowing in the nasal cannula 1c flows, and can measure the actual flow rate of the oxygen-enriched gas flowing in the nasal cannula 1c. Besides, a structure of measuring the actual flow rate of the oxygen-enriched by using another structure and system may be adopted.

Further, by realizing the so-called demand regulator function in which the breath of the patient is detected, the oxygen-enriched gas is supplied only in an aspiratory period (air is inspired) and the supply is stopped in an expiratory period (air is expired), the breath synchronizing part 8 saves (conserves) the amount of the oxygen-enriched gas supplied to the patient while an influence is not exerted on the inhalation of the patient, and consequently, in an operation mode in which an AC power source is a power supply source, use electric energy can be reduced, and in an operation mode in which a rechargeable battery is a power supply source, an operation time to next charging can be prolonged.

Incidentally, the oxygen concentrating apparatus 1 includes an operation switch (not shown) to switch between an operation mode (hereinafter also referred to as a synchronous mode) to supply the oxygen-enriched gas only in the aspiratory period by detecting the breath of the patient as stated above and an operation mode (hereinafter also referred to as a continuous mode) to always supply the oxygen-enriched gas at a constant flow rate irrespective of the breath of the patient. For example, at the time of sleep, this operation switch is operated without fail and the inhalation of the oxygen-enriched gas is performed in the continuous mode. This is adopted in order to continue the supply of the oxygen-enriched gas even in the case where the patient at the time of sleep performs the breath through the oral cavity, not the nasal cavity and the breath is not detected.

A specific structure for detecting the breath of the patient can be realized by, for example, a structure as disclosed in JP-A-2002-272845 filed by the present applicant, in which after a sound signal (breath sound of the patient) is converted into an optical signal by using an optical microphone, it is converted into a voltage signal and is further converted into a frequency so that analysis in a frequency region is performed, and the breath is detected by a difference in frequency band, a method as disclosed in JP-A-62-270170 in which a sensor made of a pyroelectric element is provided in a nasal cannula, a structure as disclosed in JP-B-5-71894 in which a pressure detector is used to detect electrostatic capacity by using a high molecular film of laminated conductive layers and by a diaphragm pressure meter, a method as disclosed in JP-A-2-88078 in which a pressure detector is provided in the vicinity of an oxygen supply port of an oxygen concentrating apparatus main body, and supply of an oxygen-enriched gas is controlled based on the signal of the pressure detector, or the other method.

A display part 10 is display means including a display member such as a liquid crystal panel and a peripheral interface part, and displays information transmitted from the main control part 14 on the display member. The content of data displayed by the display part 10 includes, in addition to the content displayed in a conventional oxygen concentrating apparatus, such as a display of an operation on state, a display of warning or alarm, and a display of a set flow rate, as described later, information of a history of a supply condition under which the oxygen-enriched gas is supplied, patient's compliance information to indicate the patient observance tendency of prescription instruction, which is obtained by comparing the history information of the supply condition with prescription content, and the like. The specific content of the patient's compliance information will be described later.

An information output end 11 is an output terminal or a transmission interface to transmit various information transmitted from the main control part 14 to an apparatus outside the oxygen concentrating apparatus 1, for example, a personal computer through a wireless or wired transmission path, and may be a structure based on RS-232C, USB, Bluetooth or other well-known communication standards. The information to be transmitted includes, in addition to the content displayed in a conventional oxygen concentrating apparatus, as described later, the information of the history of the supply condition under which the oxygen-enriched gas is supplied, the patient's compliance information obtained by comparing the information of the history of the supply condition with the prescription content, and the like.

A flow rate setting part 12 is operated by the user such as the patient and is for setting the flow rate of the oxygen-enriched gas to be supplied, and for example, a dial switch is rotation operated, and when a desired selection value is selected from 1 liter/minute, 2 liters/minute, 3 liters/minute and the like, the main control part 14 having detected this selection value controls the compressor 4, the operation speed of the adsorption unit 5 and the like, and realizes the set desired flow rate.

The compressor 4 includes a compressor drive motor to drive the compressor 4, and the compressor drive motor rotation drives the compressor 4 in accordance with the drive current generated and outputted by the power source control part 3 so that the rotation number set by the main control part 14 is realized. A compression mechanism part of the compressor 4 is for compressing the air by the rotation force obtained by the compressor drive motor, and there are various kinds according to the compression system, and a reciprocating motion piston type, a rotation scroll type or the like is generally often used. However, as long as the atmospheric air can be compressed, any type may be used.

In addition to the drive current output to drive the compressor 4 as described above, the power source control part 3 has the function to supply electric power to the respective components included in the apparatus 1.

Incidentally, in the oxygen concentrating apparatus 1 of this embodiment, as characteristic points for realizing a transportable and portable structure, a power supply method from only a home AC power source in a conventional typical fixed installation type oxygen concentrating apparatus is improved, and a three-way power source system is adopted which includes a built-in battery, a home AC power source, and a vehicle-mounted DC power source. Thus, a power source input end 2 is provided at the housing outer peripheral part facing the outside of the apparatus, and DC electric power can be received through this from an AC power source unit 15 or a vehicle-mounted power source unit 16 connected to a cigar lighter contact in an automobile.

Further, a repeatedly rechargeable battery 13 is detachably provided inside the oxygen concentrating apparatus 1, and in the case where power supply through the power source input end 2 can not be performed, electric power is supplied to the power source control part 3 by discharge from the battery 13.

Incidentally, charging to the battery 13 is generally executed in such a manner that while the battery 13 is mounted in the oxygen concentrating apparatus 1, electric power supplied from the AC power source unit 15 or the vehicle-mounted power source unit 16 is supplied via the power source input end 2 and the power source control part 3.

The main control part 14 includes not only a function, which is similar to that of a conventional structure oxygen concentrating apparatus, to control the respective components of the oxygen concentrating apparatus 1 to supply the oxygen-enriched gas, but also a function to record and hold, at the time of supply and whenever necessary, information (hereinafter also referred to as supply history information) of a history of a supply condition under which the oxygen-enriched gas is supplied, a function to generate patient's compliance information which is obtained by comparing the supply history information with the prescription content of the oxygen therapy of the patient previously stored in the main control part 14 and is information to indicate the degree to which the patient performs the oxygen inhalation of the home oxygen therapy as prescribed or the observance tendency of the prescription instruction, a function to output at least one of the supply history information and the patient's compliance information obtained in this way through the information output end 11 to an apparatus outside the oxygen concentrating apparatus 1, for example, a personal computer, or to output it to the display part 10 or the other display means and to cause a display, and the like. These functions will be described later.

Besides, as a characteristic structure for realizing the transportable and portable function, in addition to the previously described points, the oxygen concentrating apparatus 1 of this embodiment includes, for example, a housing part having a necessary degree of dust proof and water proof function and protecting the inside of the oxygen concentrating apparatus 1, a wheel part attached to the housing part, a holding handle similarly attached to the housing part and the like (none of them are shown), and when going out, the patient can carry it by pulling or the like. A structure may be such that the wheel part is not provided, and the patient directly carry it with a sling belt, or puts it in a rucksack and shoulders it.

Further, in order to make the oxygen concentrating apparatus 1 portable, the mass and volume are greatly reduced from those in the related art. For example, a conventional fixed installation type typical oxygen concentrating apparatus has a weight of about 30 kg, however, since the apparatus 1 of this embodiment has a weight of less than 5 kg and is easily carried, the patient easily carries it to the medical institution where the patient receives regular outpatient treatment.

[Operation of the Oxygen Concentrating Apparatus]

Next, the operation of the oxygen concentrating apparatus 1 of this embodiment will be described with reference to FIG. 1 which is a connection view of the apparatus 1.

First, in the case where a patient 1b is in patent's home 1a and receives the oxygen therapy, similarly to the related art, electric power is supplied from the home AC power source, and inhalation of the oxygen-enriched gas can be performed. When the inhalation is performed by the driving of the battery 13 in the patient's home, since the patient 1b carries the apparatus 1 without restriction of the AC consent and continues the inhalation while freely moving in the patient's home, it is possible to resolve inconvenience that like a conventional fixed installation type apparatus, a cannula with a long extension tube of several meters is connected to the oxygen concentrating apparatus, and inhalation is performed through the cannula with the extension tube.

As a characteristic point of this embodiment, when the oxygen-enriched gas is supplied, the main control part 14 of the apparatus 1 continuously records and holds supply history information, which is the history of the supply condition of the oxygen-enriched gas, as the so-called journal data, together with time information, into an internal memory part (not shown) at all times or suitable timing. That is, the history information of the supply time is recorded and held.

The data included in the supply history information includes, in addition to a supply time history (history of supply time), an oxygen concentration of the supply gas, a supply flow rate, information which is detected by the breath synchronizing part 8 and indicates whether the patient 1b breathes, and the like. The information of the flow rate may be a value of a flow rate measured by the ultrasonic sensor part 7 and actually flowing in the cannula, a set specified flow rate, or both of them. Besides, together with the supply history information, the other information may be simultaneously recorded and held. The other information may be, for example, operation information of the oxygen concentrating apparatus 1 (information notifying the operation state of the compressor 4, the absorption unit 5 or the like, information indicating what supplies electric power, information of the remaining power amount of the battery 13, information of accumulated use time of the apparatus 1, information of oxygen concentration of the supply air, and the like), information as to whether the wheel part attached to the housing part rotates and the rotation speed (by this, whether the patient 1b moves while carrying the apparatus 1, and the movement speed are known), information of the present position in the case where the apparatus 1 includes position detection means such as a GPS terminal, and the like.

Alternatively, an accelerator sensor is mounted in the oxygen concentrating apparatus 1, and information relating to the movement of the oxygen concentrating apparatus 1 obtained from the accelerator sensor can be made the other information which may be simultaneously recorded. At the time of exercise, since there is a high possibility that the patient carries the oxygen concentrating apparatus 1, the movement situation of the patient can be directly grasped from the record.

Further, the supply history information, the other information, and after-mentioned patient's compliance information may be recorded and held in independently provided memory means, not the memory in the inside of the main control part 14, or alternatively, removable memory means such as a Memory Stick™ or an SD Card™ is used and at the time of going to the medical institution 2a, only the removable memory means, not the whole oxygen concentrating apparatus 1, is extracted and may be carried into the medical institution 2a. Alternatively, although the patient carries the oxygen concentrating apparatus 1 into the medical institution 2a where regular outpatient treatment is received, as a method of delivering the supply history information, the other information, and the after-mentioned patient's compliance information to an information equipment of the medical institution, the so-called medium delivery may be performed in such a manner that after the removable memory means is removed from the oxygen concentrating apparatus 1, it is attached to the information equipment of the medical institution to deliver the information.

Further, at the same time as the recording and holding of the supply history information or at a different time point, the main control part 14 of the apparatus 1 generates the patient's compliance information as data indicating the degree to which the oxygen therapy is performed as prescribed or the observance tendency of the patient to the prescription instruction, and records and holds it in the memory part of the main control part 14 or in the other memory means.

The patient's compliance information is obtained by comparing the supply history information with the prescription information of the patient previously stored in the main control part 14 or the other memory means, and various modes are conceivable. Some of them will be exemplified below.

Incidentally, in the following exemplification, information of the flow rate of the oxygen-enriched gas used for the generation of the patient's compliance information may be a flow rate set value by the flow rate setting part 12, or a flow rate measured value by the ultrasonic sensor part 7, or both of them may be written side by side. Further, based on the result of the breath detection by the breath synchronizing part 8, it may be additionally written whether the patient actually breathes, or it is possible to indicate that there is no data in the case where a breath is not detected.

Besides, the patient's compliance information described below can have various modes including a construction in which an explanation is not made, and the various modes can include information almost equal to the supply history information in addition to a mode of information directly indicating the patient's compliance of the therapy. This is because according to various environmental differences relating to the home oxygen therapy, such as characteristics of the patient and a medical plan of a medical worker, the mode of optimum information for acquiring the therapy compliance of the patient can be changed. Then, in the following description, in order to avoid the troublesomeness, with respect to the various modes in the wide range of from the information directly indicating the therapy compliance of the patient to the supply history information, the name of [patient's compliance information] is used and the description will be made.

[Example (1) of Patient's Compliance Information—Compliance Scalar Value]

This is information indicating the therapy compliance of the patient by a single or plural scalar values (numerical values), and in the case where for example, the prescription says that [inhalation should be performed every day at 1 liter/minute at the time of rest for 12 hours, 2 liters/minutes at the time of exercise for 4 hours, and 1 liter/minute at the time of sleep for 8 hours], the consistence degree is calculated based on daily actual supply history information and a specified calculation method, and the value is made, for example, [compliance of 88%]. In this mode, since it is not necessary to read a diagram such as a graph, and the goodness of the compliance can be instantaneously understood, in outpatient treatment in which a medical examination time for one patient is limited, the medical worker can effectively grasp the compliance of the patient.

With respect to the calculation method of the scalar value, some examples will be described below. Incidentally, in these examples, the supply history information used for the calculation is data stored during days (for example, 30 days) from the last visit to the medical institution to this visit thereto.

(1-1) Average Use Time Per Day

This is a calculated average time per day in which the oxygen concentrating apparatus 1 is used, and indicates how many hours the patient performs the inhalation of the oxygen-enriched gas, and for example, in the case where the prescription by the medical worker indicates the inhalation of 24 hours per day, it is of course desirable that the value is close to that. Whether the apparatus 1 is used or not is judged based on whether the power source switch of the apparatus 1 is in an on state, or whether the apparatus 1 in the operation state detects the breath of the patient.

(1-2) Average Use Flow Rate

This is a value obtained by dividing the total volume of the supplied gas by the whole use time of the apparatus 1 during the hospital visit interval period (for example, 30 days), and indicates an average supply flow rate during the hospital visit interval period. Similarly, it is desirable that the value is close to the prescribed value.

(1-3) Average Exercise Ratio (Average Synchronous Use Ratio)

This is a ratio of the synchronous mode use time to all the time when the supply of the oxygen-enriched gas is performed. The synchronous mode is mainly used when the oxygen-enriched gas is supplied from the oxygen concentrating apparatus 1 by battery driving, and in almost all cases, the patient performs an action such as going out, working or walking, and accordingly, the medical worker can grasp the ratio of the exercise time to all the inhalation time, that is, the tendency of action of the patient.

(1-4) Average Synchronous Flow Rate

This is an average value of the supply flow rate in the case where the synchronous mode is used. This is desirable to be close to the prescribed use flow rate at the time of exercise.

(1-5) Average Continuous Flow Rate

Similarly, this is an average value of the supply flow rate in the case where the continuous mode is used. This is desirable to be close to the prescribed use flow rate at the time of rest and at the time of sleep.

(1-6) Breath Sensing Ratio

This is a ratio of a time when the breath of the patient is detected (sensed) to all the time when the oxygen concentrating apparatus 1 is in an operation state (state in which the oxygen-enriched gas is supplied). Since the apparatus 1 of this embodiment always continuously detects the breath of the patient irrespective of the synchronous mode or the continuous mode, this value can be calculated. In the case where this value is large, it is conceivable that a situation is such that the patient breathes through the oral cavity, not the nasal cavity, and the oxygen-enriched gas is not correctly inhaled, or although the apparatus 1 is in a drive state, for example, a cannula is not mounted and the patient does not perform the inhalation, and in any case, the correction is needed.

(1-7) Exercise Time Breath Sensing Ratio

Similarly, this is a ratio of a time when the breath of the patient is detected (sensed) to all the time when the oxygen concentrating apparatus 1 is in the synchronous mode and is in the state where the oxygen-enriched gas is supplied, and it is possible to detect a state (breath through the oral cavity, or the like) in which the oxygen-enriched gas is not correctly inhaled at the time of exercise.

(1-8) Apparatus Nonuse Day Count

This is the number of days, during the hospital visit interval period (for example, 30 days), obtained by adding days when the power source of the oxygen concentrating apparatus 1 is never turned on, or the supply of the oxygen-enriched gas is never performed. The therapy compliance of the patient can be directly grasped. Besides, in addition to the calculation of the scalar value as described above, the patient's compliance information may be made a mode in which intuitive and quick grasp can be made by imitating the traffic light colors of red, yellow, blue and the like.

[Example (2) of Patient's Compliance Information— Change Trend Value of Compliance Scalar Value]

This is for grasping a trend, by using the differential or the like, of a daily change of values obtained by calculating the above-described compliance scalar value every day, for example, numerical values of the daily use time, use flow rate, exercise ratio or the like, and it is possible to instantaneously understand whether the compliance of the patient is increasing or decreasing.

[Example (3) of Patient's Compliance Information—Intraday Change Trend Graph of Compliance Scalar Value]

Similarly, this is such that the daily change of the values obtained by calculating the above-described compliance scalar value every day, for example, the numerical values of the daily use time, use flow rate, exercise ratio or the like is made a change graph (for example, a line graph) at every time in a specific day or in an averaged day, and it is understood that for example, the time of nonuse of the oxygen concentrating apparatus 1 of a certain patient is concentrated on a specific time in the daytime.

[Example (4) of Patient's Compliance Information—Journal Data with Prescription Information]

This is such that measured data, such as a change of a flow rate in a day or every day in a month or detection result of breath, is directly made a band graph or a line graph in contradistinction to time, and the prescription value is also displayed. This is effective in that the journal data can be minutely investigated and carefully read while being compared with the prescription value. It is convenient to perform classification by color for the respective flow rates.

Incidentally, it is effective that the various compliance information described above is made information indicating the state of change in a specified period, such as, for example, the intraday change graph. Here, the specified period is a day, a week, a month, a year, or an arbitrary set period.

Further, it is also effective to structure such that the change of the various compliance information as described above is indicated in a specified period unit, for example, a day unit, and the state of the change of the compliance information with the passage of time is displayed. Similarly to the above, this specified period is a day, a week, a month, a year, or an arbitrary set period. By adopting the structure as stated above, the usage can be effectively made for the grasp of the clinical state of the patient and its change.

The patient's compliance information is generated based on not only the supply history information in the patient's home 1a but also that at a place 3a where the patient has gone. Then, in the day of a hospital visit which is made regularly, for example, once a month, the patient 1b carries the oxygen concentrating apparatus 1 to visit the medical institution, a doctor 2b of the medical institution 2a causes the display part 10 of the apparatus 1 to display the patient's compliance information of the above-mentioned structure or the other structure and confirms it, or causes a personal computer connected to the information output end 11 through a transmission cable 2e to display it and confirms it, and consequently, from the objectively correct viewpoint, it is possible to grasp whether the patient correctly receives the home oxygen therapy, and the therapy effect of the home oxygen therapy can be greatly improved.

When the patient's compliance information is displayed on a medical institution terminal 2c of the medical institution, by the function of a dedicated display program previously installed in the medical institution terminal 2c, first, a menu screen (not shown) is displayed on the display screen of the medical institution terminal 2c, a desired item name is selected from item names included on this menu screen, for example, the foregoing ⌈average use time per day⌋ and ⌈average use flow rate⌋, and can be displayed on the display screen of the medical institution terminal 2c. The display sequence of the item names on the menu screen may be made the display frequency sequence to improve the efficiency of selection work.

Incidentally, at least one of the supply history information and the patient's compliance information may be outputted to the outside of the apparatus 1 or may be displayed by display means. Besides, in order to protect the privacy of the patient or to prevent the information from being modified by the patient, the structure may be made such that a lock is released by authentication confirmation using a password or the like or a physical key so that only a previously appointed medical worker can execute the readout, display, or reset (erase) operation of the supply history information, the patient's compliance information and the like. For that purpose, a key is provided at the side of the oxygen concentrating apparatus 1, or the main control part 14 may be constructed such that only in the case where a correct password is sent from the medical institution terminal 2c connected to receive information, the information is transmitted and displayed.

The observed or read supply history information and the patient's compliance information are stored and held in a personal computer or a server, and can be used for later medical care, or can be used for an electric medical chart, or a participating doctor 4b of a participating medical institution 4a, who examines the patient 1b in corporation with the doctor 2b of the medical institution 2a, performs browsing (perusal) or reading from a second personal computer through an Internet network 5a and can easily use it for the participating medical care.

Further, for example, information relating to the operation state of the oxygen concentrating apparatus 1 recorded and held simultaneously with the supply history information is read into the personal computer 2c of the medical institution at the time of a hospital visit of the patient, and a check is performed by a dedicated check program, so that the abnormality of the apparatus 1 can be quickly detected, and the structure in which the maintenance of the oxygen concentrating apparatus 1 becomes very easy and effective can also be sufficiently realized.

For example, the oxygen concentration of the supplied oxygen-enriched gas is continuously measured and recorded, and in the case where the lowering tendency of the oxygen concentration is seen, an alarm display is performed, so that a medical worker or the like can give an instruction of maintenance to check the contamination of a filter of an air inlet. Alternatively, in the case where the flow rate in the nasal cannula 1c is lower than a normal value although the supply pressure of the oxygen-enriched gas is normal in the oxygen concentrating apparatus 1, there is a fear that the nasal cannula 1c is bent halfway and a jet of gas is blocked, and accordingly, the medical worker informed of this situation by an alarm again guides the patient in the handling of the nasal cannula 1c at the time of inhalation, especially at the time of sleep, and can make the correction.

EFFECTS OF THE INVENTION

The invention can provide an oxygen concentrating apparatus which enables a medical worker to certainly and easily know whether a patient on a home oxygen therapy, who continues to inhale an oxygen-enriched gas at home, performs the inhalation as prescribed, and an execution support method of the home oxygen therapy.

The invention claimed is:

1. An oxygen concentrating apparatus which separates atmospheric oxygen to supply an oxygen-enriched gas to a user, the oxygen concentrating apparatus comprising:
   an oxygen concentrating means for obtaining the oxygen-enriched gas by separating and concentrating atmospheric oxygen;
   a detecting means for detecting presence/absence of breathing of the user;
   a controlling means for controlling in such a manner that the oxygen enriched gas is supplied only during an inspiration period by a signal from the detecting means;
   a recording means for recording supply history information which is a history of a supply condition of the oxygen-enriched gas supplied to the user; and
   an output means and/or display means for sending and/or displaying the supply history information that has been recorded.

2. An oxygen concentrating apparatus which separates atmospheric oxygen to supply an oxygen enriched gas to a user, the oxygen concentrating apparatus comprising:
   an oxygen concentrating means for obtaining the oxygen-enriched gas by separating and concentrating atmospheric oxygen;
   a detecting means for detecting presence/absence of breathing of the user;
   a controlling means for controlling in such a manner that the oxygen enriched gas is supplied only during an inspiration period by a signal from the detecting means;
   a recording means for recording supply history information which is a history of supply conditions of the oxygen enriched gas supplied to the user together with time information; and
   an output means and/or display means for sending the recorded supply history information to an outside of the apparatus together with the time information.

3. An oxygen concentrating apparatus which separates atmospheric oxygen to supply an oxygen enriched gas to a user, the oxygen concentrating apparatus comprising:
   an oxygen concentrating means for obtaining the oxygen-enriched gas by separating and concentrating atmospheric oxygen;
   a detecting means for detecting presence/absence of breathing of the user;
   a controlling means for controlling in such a manner that the oxygen enriched gas is supplied only during an inspiration period by a signal from the detecting means;
   a recording means for recording supply history information which is a history of supply conditions of the oxygen enriched gas supplied to the user; and
   an output means and/or display means for sending the recorded supply history information to an outside of the apparatus, wherein
   the recording means records as the supply history information (A) at least one of the supply history information including an average use time, an average use flow rate, an average exercise ratio, an average synchronous flow rate, an average continuous flow rate, a breath sensing ratio, an exercise time breath sensing ratio, and an apparatus nonuse day count or (B) a change of at least one of the supply history information including a use time, a use flow rate, an exercise ratio, a synchronous flow rate, a continuous flow rate, a breath sensing ratio, and an exercise time breath sensing ratio in a specified period or a change thereof in a specified period unit.

4. The oxygen concentrating apparatus as recited in any one of claims 1 to 3, further comprising:
   prescription supply condition input means for inputting a supply condition prescribed for the user, said oxygen concentrating apparatus having arithmetic means for calculating compliance information relating to a patient's compliance by comparing the recorded supply condition with the prescribed supply condition.

5. The oxygen concentrating apparatus as recited in any one of claim 4,
   wherein the recording means records at least one of the supply conditions including a supply flow rate set value of the oxygen-enriched gas, an actually measured value of a supply flow rate, and a history record of supply time.

6. The oxygen concentrating apparatus as recited in claim 5:
   an arithmetic calculating means for calculating information of (C) at least one of the patient's compliance information including an average use time, an average use flow rate, an average exercise ratio, an average synchronous flow rate, an average continuous flow rate, a breath sensing ratio, an exercise time breath sensing ratio, and an apparatus nonuse day count or (D) a change of at least one of the patient's compliance information including a use time, a use flow rate, an exercise ratio, a synchronous flow rate, a continuous flow rate, a breath sensing ratio, and an exercise time breath sensing ratio in a specified period or a change thereof in a specified period unit.

7. The oxygen concentrating apparatus as recited in claim 6,
   wherein the oxygen concentrating apparatus can be carried by the user and is capable of supplying the oxygen enriched air to the user at least during movement of the user.

8. The oxygen concentrating apparatus as recited in claim 7,
   wherein an authentication check of a execution operation when at least one of output display, and deletion of the supply history information or the information of (C) or (D).

9. An oxygen concentrating apparatus which separates atmospheric oxygen to supply an oxygen-enriched gas to a user, the oxygen concentrating apparatus comprising:
   an oxygen concentrating means for obtaining the oxygen-enriched gas by separating and concentrating atmospheric oxygen;
   a detecting means for detecting presence/absence of breathing of the user;
   a controlling means for controlling in such a manner that the oxygen enriched gas is supplied only during an inspiration period by a signal from the detecting means;
   a recording means for recording supply history information which is a history of a supply condition of the oxygen-enriched gas supplied to the user and the information includes a signal presence/absence of breathing of the user from the detecting means; and
   an output means and/or display means for sending and/or displaying the supply history information that has been recorded.

* * * * *